United States Patent [19]

Konai et al.

[11] E Patent Number: Re. 33,779

[45] Reissued Date of Patent: Dec. 24, 1991

[54] PREPARATION PROCESS OF 4,4-DIHYDROXYBIPHENYL

[75] Inventors: Yutaka Konai, Iwaki; Tadashi Nakamura, Kodaira; Takayuki Tanonaka, Iwaki; Kazuo Yoshida, Iwaki; Yoshihisa Machida, Iwaki, all of Japan

[73] Assignee: Kureha Kagaku Kogyo K.K., Japan

[21] Appl. No.: 569,059

[22] Filed: Aug. 13, 1990

Related U.S. Patent Documents

Reissue of:

[64] Patent No.: 4,804,788
Issued: Feb. 14, 1989
Appl. No.: 116,733
Filed: Nov. 4, 1987

[30] Foreign Application Priority Data

Nov. 7, 1986 [JP] Japan ..... 61-263841

[51] Int. Cl.[5] ..... C07C 39/14; C07C 39/15

[52] U.S. Cl. ..... 568/730; 568/741; 568/722; 568/771; 568/803

[58] Field of Search ..... 568/722, 730, 741, 771, 568/803

[56] References Cited

U.S. PATENT DOCUMENTS

| | | | |
|---|---|---|---|
| 3,812,445 | 5/1974 | Stefani | 339/32 |
| 3,813,454 | 5/1974 | Massie | 568/730 |
| 4,174,460 | 11/1979 | Seifert et al. | 568/771 |
| 4,205,187 | 5/1980 | Cardena et al. | 568/730 |
| 4,243,822 | 1/1981 | Demler et al. | 568/722 |
| 4,475,000 | 10/1984 | Pendery et al. | 568/730 |
| 4,482,755 | 11/1984 | Kruse et al. | 568/730 |
| 4,487,978 | 12/1984 | Kruse et al. | 568/730 |
| 4,551,562 | 11/1985 | Drauz | 568/771 |
| 4,564,713 | 1/1986 | Imanari et al. | 568/730 |
| 4,804,788 | 2/1989 | Konai et al. | 568/730 |

FOREIGN PATENT DOCUMENTS

| | | | |
|---|---|---|---|
| 3204079 | 8/1983 | Fed. Rep. of Germany | 568/730 |
| 0036153 | 5/1973 | Japan | 568/730 |
| 0091238 | 2/1975 | Japan | 568/730 |
| 0068154 | 6/1977 | Japan | 568/730 |
| 0112844 | 9/1979 | Japan | 568/730 |
| 0128726 | 9/1979 | Japan | 568/730 |
| 0017304 | 2/1980 | Japan | 568/730 |
| 0053631 | 5/1981 | Japan | 568/730 |
| 0057728 | 5/1981 | Japan | 568/730 |
| 0018329 | 2/1983 | Japan | 568/730 |
| 0018330 | 2/1983 | Japan | 568/730 |
| 0189127 | 11/1983 | Japan | 568/730 |
| 0001434 | 1/1984 | Japan | 568/730 |
| 00233338 | 2/1985 | Japan | 568/730 |
| 0013451 | 4/1986 | Japan | 568/730 |
| 2176188 | 1/1986 | United Kingdom | 568/730 |

OTHER PUBLICATIONS

J. Org. Chem., v. 15, M. S. Kharasch et al.; pp. 748–752 (1950).

*Primary Examiner*—Werren B. Lone
*Attorney, Agent, or Firm*—Lowe, Price, LeBlanc & Becker

[57] ABSTRACT

4,4'-Dihydroxybiphenyl is prepared by decomposing 4,4'-di(2-hydroxy-2-propyl)biphenyl with hydrogen peroxide and an acid catalyst in acetonitrile as a solvent. Especially, this process minimizes the formation of by-products and permits easy purification of the intended product.

2 Claims, No Drawings

PREPARATION PROCESS OF 4,4-DIHYDROXYBIPHENYL

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a novel process for the preparation of 4,4'-dihydroxybiphenyl. 4,4'-Dihydroxybiphenyl is a compound useful industrially as a starting monomer for heat-resistant polymers which have drawn attention in recent years. For example, ternary copolyesters containing p-hydroxybenzoic acid, terephthalic acid and 4,4'-dihydroxybiphenyl as their components include a sort of so-called hermotropic liquid crystalline polymers, which have found actual utility as melt-processable heat-resistant materials for tableware which can be heated in a cooking oven.

2. Related Art

As preparation processes for 4,4'-dihydroxybiphenyl, numerous processes have heretofore been proposed as will be described below.

(1) 2,6-Di-tert-butylphenol is subjected to oxidative dimerization, followed by reduction and dealkylation [J. Org. Chem., 34, 1160 (1969); Japanese Patent Laid-Open No. 11238/1976; ibid, 189127/1983; ibid., 23338/1985; U.S. Pat. No. 4,205,187].

(2) Similar to the above process (1). Transalkylation of phenol with an alkylbenzene is effected instead of the dealkylation (Japanese Patent Laid-Open No. 1434/1984; U.S. Pat. No. 4,482,755; ibid., 4,487,978).

(3) Biphenyl is subjected to sulfonation and alkali fusion (Japanese Patent Laid-Open No. 68154/1977; ibid., 112844/1979; ibid., 57728/1981; ibid., 128726/1981; ibid., 18329/1983; ibid., 18330/1935; U.S. Pat. No. 4,243,822; West German Pat. No. 3,204,079).

(4) Biphenyl is halogenated, followed by hydrolysis (Japanese Patent Publication No. 13451/1986; Japanese Patent Laid-Open No. 17304/1980; U.S. Pat. No. 4,475,000).

(5) Phenol is dimerized (U.S. Pat. No. 3,812,445; ibid., 3,813,445).

(6) Phenol is converted into dihydroxybiphenylsulfon, followed by alkali fusion (Japanese Patent Laid-Open No. 36153/1973).

(7) A halogenated phenol is dehalogenated, followed by dimerization (Japanese Patent Laid-Open No. 53631/1981).

4,4'-Dihydroxybiphenyl can be prepared by using any one of the processes listed above. These processes are however hardly considered to be satisfactory fully as industrial preparation processes.

Namely, the processes (1) and (2) include many steps and are hence complex. Moreover, the reagent or catalyst employed in the dealkylation or transalkylation step is costly, and an irksome purification procedure is required after the completion of the reaction because the removal of the catalyst and the like is difficult.

The process (3) has a problem in the treatment of waste water from the alkali fusion and is not desirable from the environmental standpoint. In addition, the process (3) cannot selectively prepare the 4,4'-derivative alone and thus requires a troublesome purification step.

The process (4) cannot selectively form the 4,4'-derivative alone. A heavy metal compound is often used in the hydrolytic step, leading also to difficult purification.

The process (5) uses a strong acid as a catalyst at an elevated temperature of 225° C. or higher. A reactor of a special material is hence needed.

Likewise the process (3), the process (6) has a problem in the treatment of waste water from the alkali fusion.

In the process (7), the selectively of the dimerization reaction is so low that this process can hardly be practised unless byproduced phenol is used effectively.

The above-described processes which have heretofore been proposed as preparation processes for 4,4'-dihydroxybiphenyl are accompanied by their own drawbacks as mentioned above. A great deal of efforts has been exercised with a view toward making improvements thereto. No significant effects have however been achieved. Accordingly, the high price of 4,4'-dihydroxybiphenyl still remains as an obstacle for the expansion of its application field.

SUMMARY OF THE INVENTION

An object of this invention is therefore to overcome the above-described drawbacks of the prior art processes for the preparation of 4,4'-dihydroxybiphenyl and hence to develop a process for preparing 4,4'-dihydroxybiphenyl, which permits selective preparation of the 4,4'-derivative alone and features its easy purification.

Another object of this invention is to provide a process for preparing 4,4'-dihydoxybiphenyl by using 4,4'-di(2-hydroxy-2-propyl)biphenyl as a starting material. Use of the latter compound has not been contemplated of in the prior art.

The above objects of this invention can be attained by decomposing 4,4'-di(2-hydroxy-2-propyl)biphenyl with hydrogen peroxide and an acid catalyst in acetonitrile as a solvent. According to this process, the 4,4'-derivative alone can be prepared and high-quality 4,4'-dihydroxybiphenyl permitting easy purification can be obtained.

DETAILED DESCRIPTION OF THE INVENTION

Features of the present invention will hereinafter be described in detail.

(Starting material, i.e., 4,4'-di(2-hydroxy-2-propyl)-biphenyl)

In the process of this invention, 4,4'-di(2-hydroxy-2-propyl)biphenyl is used as a starting material, 4,4'-Di(2-hydroxy-2-propyl)biphenyl can be obtaind easily in a high purity of 99.8% or higher by distillating a mixture, which has been obtained by propylating and transalkylating biphenyl and has a high diisopropylbiphenyl content, to separate diisoropylbiphenyls therefrom, crystallizing out 4,4'-diisopropylbiphenyl from the diisopropylbiphenyls by making use of differences in crystallinity, and then oxidizing the 4,4'-diisopropylbiphenyl with molecular oxygen in the presence of an aqueous alkali solution in an oxidation reactor made of nickel at parts thereof where the oxidation reactor comes into contact with a reaction mixture. (Solvent)

Upon practice of the process of this invention, acetonitrile is used as a solvent in an amount 3–50 times [[volume (ml)/weight (g)]] (*volume (ml)/weight(g)*) as much as the starting material, i.e., 4,4'-di(2-hydroxy-2-propyl)biphenyl. If the solvent should be used in any amounts smaller than the lower limit, the elimination of reaction heat cannot be performed smoothly. On the other hand, any amounts exceeding the upper limit will require a high cost for the recovery and reutilization of the solvent, whereby the process will be rendered inappropriate for industrial practice. (Acid catalyst)

Upon practice of the process of this invention, an inorganic acid such as sulfuric acid or perchloric acid, an organic acid such as trifluoroacetic acid or a solid acid such as cation-exchange resin is used as an acid catalyst. Although the amount of the acid catalyst to be used varies depending on the concentration of the starting material, i.e., 4,4'-di(2-hydroxy-2-propyl)biphenyl, the concentration of hydrogen peroxide and the concentration of water reaction temperature, the acid catalyst is used in an amount of 0.0005-2 times (by weight) the starting material in the case of an inorganic acid or organic acid and in an amount of 0.01-5 times (by weight) the starting material in the case of a solid acid. If the acid catalyst should be used in any amounts smaller than the lower limit, it will be difficult to complete the reaction. On the other hand, any amounts in excess of the upper limit will lead to an unduly high cost for the catalyst so that the process will be rendered no longer suitable for industrial practice. (Hydrogen peroxide)

Hydrogen peroxide is used in an amount of 2–3 times (by molar ratio) as much as the starting material, i.e., 4,4'-di(2-hydroxy-2-propyl)biphenyl upon practice of the process of this invention. If hydrogen peroxide should be used in any amounts smaller than the lower limit, the starting material will not be used up. On the other hand, any amounts greater than the upper limit will result in considerable coloration of the resulting 4,4'-dihydroxybiphenyl. It is thus not preferable to use hydrogen peroxide in any amounts outside the above range. (Reaction conditions)

Upon practice of the process of this invention, the starting material, i.e., 4,4'-di(2-hydroxy-2-propyl)biphenyl, hydrogen peroxide and acetonitrile are mixed first of all. Thereafter, an acid catalyst is added to initiate a reaction. Here, the acid catalyst may be added as a solution in the above-mentioned solvent. The starting material may be or may not be dissolved completely depending on the temperature. The reaction is allowed to proceeds irrespective of the degree of dissolution of the starting material. Upon completion of the reaction, 4,4'-dihydroxybiphenyl is obtained as a homogeneous solution. If the acid catalyst should be added firstly to 4,4'-di(2-hydroxy-2-propyl)biphenyl in a state free of hydrogen peroxide, a dehydration reaction will proceed to lower the yield of 4,4'-dihyroxybiphenyl. This is certainly not preferred.

The reaction temperature is set within a range of from 20° C. to the boiling point of the solvent upon practice of the process of this invention. The reaction is usually carried out under atmospheric pressure. Since water is formed by the reaction and the reaction heat is large, it may also be feasible to conduct the reaction under reduced pressure so that both water and heat may be removed. If the reaction temperature should be lower than the lower limit, the reaction velocity will be reduced so that the catalyst will be required in a large amount. This will certainly disadvantageous from the economical standpoint. If the reaction should be effected at any temperature higher than the boiling point of the solvent, more byproducts will be formed so that the purification of the intended compound will be rendered difficult. It is hence not preferable to use such a high reaction temperature.

After completion of the reaction, the recovery of 4,4'-dihydroxybiphenyl from the reaction mixture may be carried out in various ways. 4,4'-dihydroxybiphenyl can be obtained in a crude form, for example, by adding a saturated aqueous saline solution to the reaction mixture to separate same into an organic phase and a water phase, washing the organic phase further with a saturated aqueous saline solution separating and collecting the organic phase, and then distilling off the solvent.

Crude 4,4'-dihydroxybiphenyl can be purified by recrystallization. As a recrystallizing solvent, acetonitrile, methanol, acetone or the like is suitable. Since 4,4'-dihydroxybiphenyl precipitates as high-purity crystals when the crude 4,4'-dihydroxybiphenyl is dissolved under heat in such a solvent, the resultant solution is filtered and the filtrate is cooled, the crystals are collected by filtration, washed and then dried into a final product.

ADVANTAGES OF THE INVENTION

The process of this invention is superior to the conventional processes in that it can fulfill all the following merits: (1) the starting material is readily available, (2) no monohydroxy derivatives are contained practically, (3) Dihydroxy derivatives other than the 4,4'-derivative are not contained practically, (4) the yield is substantially stochiometric, and (5) the purification of 4,4'-dihydroxybiphenyl obtained after the reaction is easy. The process of this invention is therefore useful from the industrial viewpoint.

EMBODIMENTS OF THE INVENTION

The process of this invention will hereinafter be described specifically by the following Examples and Referential Examples. Needless to say, the present invention is not necessarily limited to the following Examples.

REFERENTIAL EXAMPLE 1

Preparation of 4,4'-diisopropylbiphenyl

In an autoclave made of SUS, having an internal capacity of 1,000 ml, and fitted with a gas inlet tube, a thermometer sheath, a sampling tube and a stirrer, were charged 500 g (3.24 moles) of biphenyl and 50 g of a silica-alumina catalyst. The autoclave was heated. After the internal temperature of the autoclave had exceeded 80° C., the stirring was started and at 200° C., the feeding of propylene gas from a gas cylinder was initiated. The stirring was continued at an autoclave internal pressure of 2 kg/cm$^2$ and internal temperature of 230° C. The reaction mixture was sampled periodically to analyze its composition by gas chromatography. When the reaction has been allowed to proceed for 5 hours and the average propylation degree has reached about 2, the feeding of propylene was terminated to finish the reaction. The reaction mixture collected subsequent to cooling had the following composition:

| Components | Proportion (mole %) |
|---|---|
| Biphenyl | 3 |
| Monoisopropylbiphenyls | 24 |
| Diisopropylbiphenyls | 50 |
| (including 4,4'-diisopropylbiphenyl | 29) |

-continued

| Components | Proportion (mole %) |
|---|---|
| Triisopropylbiphenyls | 16 |
| High boiling-point products | 7 |

The whole reaction mixture was fractionated to obtain about 60 g of a fraction (168°-170° C./5 mmHg), which contained at least 48 g of 4,4'-diisopropylbiphenyl. The crude product was recrystallized twice from ethanol, whereby 30 g of crystals of 4,4'-diisopropylphenyl (m.p. 64°-65° C.; 0.126 mole; yield: 3.9% based on biphenyl) was obtained. No impurities were detected from the crystals with gas chromatography.

REFERENTIAL EXAMPLE 2

Transalkylation

Charged in the reactor employed in Referential Example 1 were 600 g of an isopropylated biphenyl mixture of a composition given below and 50 g of silica-alumina. The contents were stirred at 280° C. for 3 hours to conduct their transalkylation. Results will be shown next (numerals will be by "mole %").

| Components | Before reaction | After reaction |
|---|---|---|
| Biphenyl | 2.7 | 2.5 |
| Monoisopropylbiphenyls | 26.0 | 24.8 |
| Diisopropylbiphenyls | 46.7 | 50.0 |
| (including 4,4'-diisopropylbiphenyl) | (1.1) | (7.0) |
| Triisopropylbiphenyls | 17.8 | 15.7 |
| High boiling-point products | 6.8 | 7.0 |

It is hence clear that the content of 4,4'-diisopropylbiphenyl increased by the transalkylation.

REFERENTIAL EXAMPLE 3

Preparation of 4,4'-di(2-hydroxy-2-propyl)biphenyl

In an autoclave made of SUS316, having an internal capacity of 1,500 ml, lined with nickel and fitted with a stirrer, a gas inlet tube, a thermometer sheath, a gas outlet tube equipped with a reflux condenser, and a pressure gage, were charged 79.8 g (0.335 mole) of 4,4'-diisopropylbiphenyl, 240 g of sodium hydroxide and 560 g of water. The internal temperature was raised to 120° C., at which the contents were reacted for 22 hours while agitating them vigorously and feeding oxygen at a rate of 4,000 ml per hour (STP) while maintaining the internal pressure at 3 kg/cm$^2$G. After completion of the reaction, the contents were taken out of the autoclave and filtered to separate a colorless solid matter and an aqueous alkali phase from each other. The solid matter was washed with water to remove carboxylic acids and was then dried to obtain 78.5 g of a colorless solid substance. As a result of an analysis with high-performance liquid chromatography, the solid substance was found to contain 5.1 g (0.021 mole; conversion: 93.7%) of 4,4'-diisopropylbiphenyl, 28.3 g (0.111 mole; yield: 33.1 mole %) of 4-(2-hydroxy-2-propyl)-4'-isopropylbiphenyl, and 43.3 g (0.160 mole; yield: 47.8 mole %) of 4,4'-di(2-hydroxy-2-propyl)biphenyl. The yields of acetyl derivatives and hydroxyperoxides were all not higher than 0.1 mole %. The solid substance was recrystallized in its entirety from toluene, thereby obtaining 35.4 g of 4,4'-di(2-hydroxy-2-propyl)biphenyl (purity: 99.8%; m.p. 168°-169° C.; 0.131 mole; recovery rate of the recrystallization: 82%).

EXAMPLE 1

While stirring at 30° C., 100 mg (0.370 mmol) of 4,4'-di(2-hydroxy-2-propyl)biphenyl together with 2 ml of acetonitrile and 44 mg of 60% aqueous hydrogen peroxide solution, 50 mg of 70% perchloric acid was added dropwise. After stirring for 30 minutes, an internal standard substance was added to the reaction mixture, followed by quantitative analysis with high-performance liquid chromatography. Formation of 67.5 mg (0.362 mmol; yield: 97.8 mole %) of 4,4'-dihydroxybiphenyl was confirmed.

EXAMPLE 2

A reaction was carried out in the same manner as in Example 1 except that 20 mg of concentrated sulfuric acid was used as an acid catalyst in place of perchloric acid. A quantitative analysis of the reaction mixture with high-performance liquid chromatography confirmed the formation of 64.0 mg (0.344 mmol; yield: 92.9 mole %) of 4,4'-dihydroxybiphenyl.

EXAMPLE 3

While stirring at 25° C. 5.0 g (18.9 mmol) of 4,4'-di(2-hydroxy-2-propyl)biphenyl together with 100 ml of acetonitrile and 4.41 g of 31% aqueous hydrogen peroxide solution, 2.66 g of 70% perchloric acid dissolved in 17 ml of acetonitrile was added at once. After stirring for 40 minutes, 50 ml of acetonitrile was added to the reaction mixture and the resultant mixture was washed three times with 30-ml portions of a saturated aqueous saline solution. Acetonitrile was distilled off from the organic layer. After drying the residue at 40°-50° C. under reduced pressure to remove the remaining water, the residue was dissolved in 100 ml of acetonitrile and undissolved sodium chloride was filtered off. Acetonitrile was distilled off from the filtrate to dry the filtrate, thereby obtaining 3.20 g (17.2 mmol; 92.9 mole %) of crude 4,4'-dihydroxybiphenyl of a pale brown color. The whole product was recrystallized from 18 ml of acetone to obtain 1.34 g (m.p. 282°-283° C.) of colorless 4,4'-dihydroxybiphenyl crystals.

What is claimed is:

1. A process for the preparation of 4,4'-dihydroxybiphenyl, which comprises decomposing 4,4'-di(2-hydroxy-2-propyl)biphenyl at a reaction temperature in a range of from 20° C. to the boiling point of acetonitrile with 2-3 times (in molar ratio) of hydrogen peroxide and 0.005-5 times (in weight ratio) of an acid catalyst in [2-3 volumes/weights of] acetonitrile as a solvent *in an amount of 3-50 times (volume (ml)/weight (g)) based on the 4,4'-di(2-hydroxy-2-propyl)biphenyl.*

2. The process as claimed in claim 1, wherein the 4,4'-di(2-hydroxy-2-propyl)biphenyl and hydrogen peroxide are mixed with the acetonitrile as the solvent and the acid catalyst is added thereafter.

* * * * *